United States Patent
Meineke et al.

(10) Patent No.: US 11,131,736 B2
(45) Date of Patent: Sep. 28, 2021

(54) RETROSPECTIVE CORRECTION OF FIELD FLUCTUATIONS IN MULTIPLE GRADIENT ECHO MRI

(71) Applicant: KONINKLIJKE PHILIPS N.V., Eindhoven (NL)

(72) Inventors: Jan Jakob Meineke, Eindhoven (NL); Ulrich Katscher, Norderstedt (DE); Tim Nielsen, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 416 days.

(21) Appl. No.: 16/323,842

(22) PCT Filed: Aug. 3, 2017

(86) PCT No.: PCT/EP2017/069596
§ 371 (c)(1),
(2) Date: Feb. 7, 2019

(87) PCT Pub. No.: WO2018/029063
PCT Pub. Date: Feb. 15, 2018

(65) Prior Publication Data
US 2019/0212406 A1 Jul. 11, 2019

Related U.S. Application Data

(60) Provisional application No. 62/372,486, filed on Aug. 9, 2016.

(51) Int. Cl.
*G01R 33/561* (2006.01)
*G01R 33/24* (2006.01)
(Continued)

(52) U.S. Cl.
CPC ....... *G01R 33/5616* (2013.01); *G01R 33/243* (2013.01); *G01R 33/443* (2013.01);
(Continued)

(58) Field of Classification Search
USPC .......................................................... 324/307
See application file for complete search history.

(56) References Cited

U.S. PATENT DOCUMENTS 6,265,874 B1 7/2001 McGee et al.
6,307,369 B1 10/2001 Felmlee et al.
(Continued)

OTHER PUBLICATIONS

Funai A K et al: "Regularized Field Map Estimation in MRI",IEEE Transactions On Medical Imaging, IEEE Service Center, Piscataway, NJ, US, vol. 27, No. 10,Apr. 22, 2008 (Apr. 22, 2008), pp. 1484-1494.
(Continued)

*Primary Examiner* — Rodney E Fuller (57) ABSTRACT

An iterative reconstruction is performed of multiple gradient echo MR imaging data to generate a reconstructed MR image (36). The iterative reconstruction uses a model (30) that links the MR imaging data and the reconstructed MR image. The model includes a parameterized magnetic field fluctuation component (32). During the performing of the iterative reconstruction, parameters of the parameterized magnetic field fluctuation component of the model are updated to optimize a cost function (40) dependent on partial derivatives of the reconstructed MR image with respect to the parameters of the parameterized magnetic field fluctuation component of the model. The image may be further processed to generate an R2* map (50), an SWI image (52), or a QSM map (54).

21 Claims, 3 Drawing Sheets

(51) Int. Cl.
*G01R 33/44* (2006.01)
*G01R 33/50* (2006.01)
*G01R 33/56* (2006.01)
*A61B 5/055* (2006.01)

(52) U.S. Cl.
CPC ............ *G01R 33/50* (2013.01); *G01R 33/56* (2013.01); *A61B 5/055* (2013.01); *G01R 33/5611* (2013.01)

(56) References Cited

U.S. PATENT DOCUMENTS

| | | | |
|---|---|---|---|
| 6,329,819 | B1 | 12/2001 | Manduca et al. |
| 2007/0110290 | A1* | 5/2007 | Chang ................ G06T 5/001 382/128 |
| 2008/0107319 | A1 | 5/2008 | Chang et al. |
| 2013/0102879 | A1 | 4/2013 | MacLaren et al. |
| 2013/0221961 | A1 | 8/2013 | Liu |
| 2015/0310639 | A1 | 10/2015 | Bilgic et al. |
| 2018/0149722 | A1* | 5/2018 | Sbrizzi ................ G01R 33/243 |
| 2018/0285695 | A1* | 10/2018 | Guo ..................... G06T 7/0012 |
| 2019/0172230 | A1* | 6/2019 | Mailhe .................. G06N 3/084 |

OTHER PUBLICATIONS

Knopp T et al "Iterative Off-Resonance and Signal Decay Estimation and Correction for Multi-Echo MRI", IEEE Transactions on Medical Imaging, IEEE Service Center, Piscataway, NJ, US, vol. 28, No. 3,Oct. 3, 2008 (Oct. 3, 2008), pp. 394-404.

Khabipova Diana et al: "A modulated closed form solution for quantitative susceptibility mapping—A thorough evaluation and comparison to iterative methods based on edge prior knowl". Neuroimage, vol. 10 7, Nov. 22, 2014 (Nov. 22, 2014), pp. 163-174.
Berkin Bilgic et al: "MRI estimates of brain iron concentration in normal aging using quantitative susceptibility mapping". Neuroimage, Elsevier, Amsterdam, NL,vol. 59, No. 3,Aug. 25, 2011 (Aug. 25, 2011), pp. 2625-2635.
Loktyushin et al "Autofocusing Based Correction of B0 Fluctuation Induced Ghosting" ISMRM 2016.
Feng et al "Improved Quantitative Susceptibility and RD Mapping by Applying Retrospective Motion Correction" Proc. Intl. Soc. Magn. Reson. Med. 23 (2015) p. 1711.
McGee et al "Image Metric Based Correction (Autocorrection) of Motion Effects . . ." Journal of Magnetic Resonance Imaging 11 p. 174-181 (2000).
Loktyushin et al "Blind Retrospective Motion Correction of MR Images" Magnetic Resonance in Med. 70 p. 1608-1618 (2013).
Aktinson et al "Automatic Compensation of Motion Artifacts in MRI" Magnetic Resonance in Med. 41, p. 163-170 (1999).
Manduca et al "Autocorrection in MR Imaging: Adaptive Motion Correction Without Navigator Echos" Autocorrection in MR Imaging, vol. 215, No. 3, p. 904-909 (2000).
Atkinson et al "Automatic Correction of Motion Artifacts in Magnetic Resonance Images Using an Entropy Focus Criterion" IEEE Transactions on Medical Imaging, vol. 16, No. 6, Dec. 1997 p. 903-910.
Moghari et al "Free-Breathing 3D Cardiac MRI Using Iterative Image-Based Respiratory Motion Correction" Magnetic Resonance in Med. 70 p. 1005-1015 (2013).
Godenschweger et al "Motion Correction in MRI of the Brain" Physics in Medicine and Biology, 61 (2016) R 32-R56.

* cited by examiner

RETROSPECTIVE CORRECTION OF FIELD FLUCTUATIONS IN MULTIPLE GRADIENT ECHO MRI

CROSS REFERENCE TO RELATED APPLICATIONS

This application is a U.S. national phase application of International Application No. PCT/EP2017/069596, filed on Aug. 3, 2017, which claims the benefit of U.S. provisional Application Ser. No. 62/372,486 filed on Aug. 9, 2016 and is incorporated herein by reference.

FIELD

The following relates generally to the magnetic resonance (MR) imaging arts, to the gradient echo (GRE) MR imaging arts and to related imaging arts such as $R_2^*$-mapping, susceptibility weighted imaging (SWI) or quantitative susceptibility mapping (QSM); and the like.

BACKGROUND

Gradient echo (GRE) magnetic resonance (MR) imaging techniques advantageously acquire high-resolution three-dimensional (3D) data in a relatively short acquisition time. However, GRE sequences lack a 180° refocusing radio frequency pulse and hence are sensitive to magnetic field inhomogeneity. Due to sensitivity to off-resonance effects, physiological fluctuations induced by breathing or other subject motion can lead to artifacts, even if the tissue of interest remains motionless for the duration of the scan. This is particularly true at long echo-times, e.g. around tens of milliseconds, such as are commonly used in GRE-based imaging techniques such as susceptibility weighted imaging (SWI) or quantitative susceptibility mapping (QSM), or $R_2^*$-mapping. The magnetic field fluctuations, as they vary in time during phase-encoding, can be corrected for using additional measurements. But this entails adding additional hardware, and/or making additions to the acquisition sequence, such as adding navigator echoes.

The following discloses new and improved systems, device, and methods.

SUMMARY

In one disclosed aspect, a non-transitory storage medium stores instructions readable and executable by a computer to perform a magnetic resonance (MR) image reconstruction method. An iterative reconstruction is performed of multiple gradient echo MR imaging data to generate a reconstructed MR image. The iterative reconstruction uses a model that links the MR imaging data and the reconstructed MR image. The model includes a parameterized magnetic field fluctuation component. During performance of the iterative reconstruction, parameters of the parameterized magnetic field fluctuation component of the model are updated to optimize a cost function dependent on partial derivatives of the reconstructed MR image with respect to the parameters of the parameterized magnetic field fluctuation component of the model. In some embodiments, the parameterized magnetic field fluctuation component comprises $e^{i\omega(r,k\ (t))T_E}$, where $T_E$ is echo time of the MR imaging data at k-space location k(t) and $\omega(r,k\ (t))$ comprise parameters of the parameterized magnetic field fluctuation component. In some embodiments, the parameterized magnetic field fluctuation component models the magnetic field fluctuation as a spatially uniform temporal magnetic field fluctuation and the parameterized magnetic field fluctuation component comprises $e^{i\omega(k(t))T_E}$, where $T_E$ is echo time of the MR imaging data at k-space location k and $\omega(k(t))$ comprises parameters of the parameterized magnetic field fluctuation component. In some embodiments, the parameterized magnetic field fluctuation component models the magnetic field fluctuation as temporally constant over a single repetition time (TR) of an MR imaging data acquisition that generated the multiple gradient echo MR imaging data.

In another disclosed aspect, an MR image reconstruction device comprises a computer and a non-transitory storage medium storing instructions readable and executable by the computer to perform an MR image reconstruction method. In the method, an iterative reconstruction of multiple gradient echo MR imaging data is performed to generate a reconstructed MR image. The iterative reconstruction uses a model that links the MR imaging data and the reconstructed MR image. The model includes a parameterized magnetic field fluctuation component having parameters that are updated during the iterative reconstruction. In some embodiments, the parameterized magnetic field fluctuation component comprises an exponential function or other function of $\omega(r,k\ (t))T_E$, where $T_E$ is echo time of the MR imaging data at k-space location k(t) and $\omega(r,k\ (t))$ comprise parameters of the parameterized magnetic field fluctuation component. In some embodiments, the parameterized magnetic field fluctuation component models the magnetic field fluctuation as a spatially uniform temporal magnetic field fluctuation; for example, the parameterized magnetic field fluctuation component may comprise a function of $\omega(k(t))T_E$, where $T_E$ is echo time of the MR imaging data at k-space location k and $\omega(k(t))$ comprises parameters of the parameterized magnetic field fluctuation component. The MR image reconstruction device may further comprise a display operatively connected with the computer, with the stored instructions further readable and executable by the computer to perform quantitative susceptibility mapping (QSM) and to display a QSM map on the display and/or further readable and executable by the computer to display the reconstructed MR image on the display.

In another disclosed aspect, an MR imaging device comprises an MR scanner configured to acquire multiple gradient echo MR imaging data, and an MR image reconstruction device as set forth in the immediately preceding paragraph operatively connected to reconstruct the multiple gradient echo MR imaging data acquired by the MR scanner.

One advantage resides in improved image quality in reconstructed multi-gradient echo (multi-GRE) magnetic resonance images.

Another advantage resides in improved robustness of reconstructed multi-gradient echo (multi-GRE) magnetic resonance images against temporal magnetic field fluctuations.

Another advantage resides in improved robustness of reconstructed multi-gradient echo (multi-GRE) magnetic resonance images against spatially uniform temporal magnetic field fluctuations.

Another advantage resides in providing one or more of the foregoing image quality and robustness advantages without requiring acquisition of additional MR imaging data.

Another advantage resides in providing one or more of the foregoing advantages using computationally efficient compensation of temporal magnetic field fluctuations.

Another advantage resides in providing one or more of the foregoing advantages in the context of $R_2^*$-mapping, susceptibility weighted imaging (SWI), and/or quantitative susceptibility mapping (QSM) which are especially sensitive to image degradation caused by temporal magnetic field fluctuations.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

In some illustrative embodiments disclosed herein, an iterative reconstruction is performed of multiple gradient echo (multi-GRE) MR imaging data to generate a reconstructed MR image. The iterative reconstruction uses a model that links the MR imaging data and the reconstructed MR image. The model includes a parameterized magnetic field fluctuation component. During the performing of the iterative reconstruction, parameters of the parameterized magnetic field fluctuation component of the model are updated to optimize a cost function dependent on partial derivatives of the reconstructed MR image with respect to the parameters of the parameterized magnetic field fluctuation component of the model.

By using a parameterized model that leverages a priori knowledge of the characteristics of the multi-GRE imaging, temporal magnetic field fluctuation compensation can be performed in a computationally efficient way. For example, the parameterized magnetic field fluctuation component may model the magnetic field fluctuation as constant over a single repetition time (TR) of the multiple gradient echo MR imaging data acquisition, in the expectation that the magnetic field fluctuation should be relatively constant over a single TR. Additionally or alternatively, the parameterized magnetic field fluctuation component may employ parameters having a linear variation along each of three orthogonal spatial axes. This provides more accurate compensation of a spatially varying temporal magnetic field fluctuation without introducing a large number of model parameters.

Figure 1:
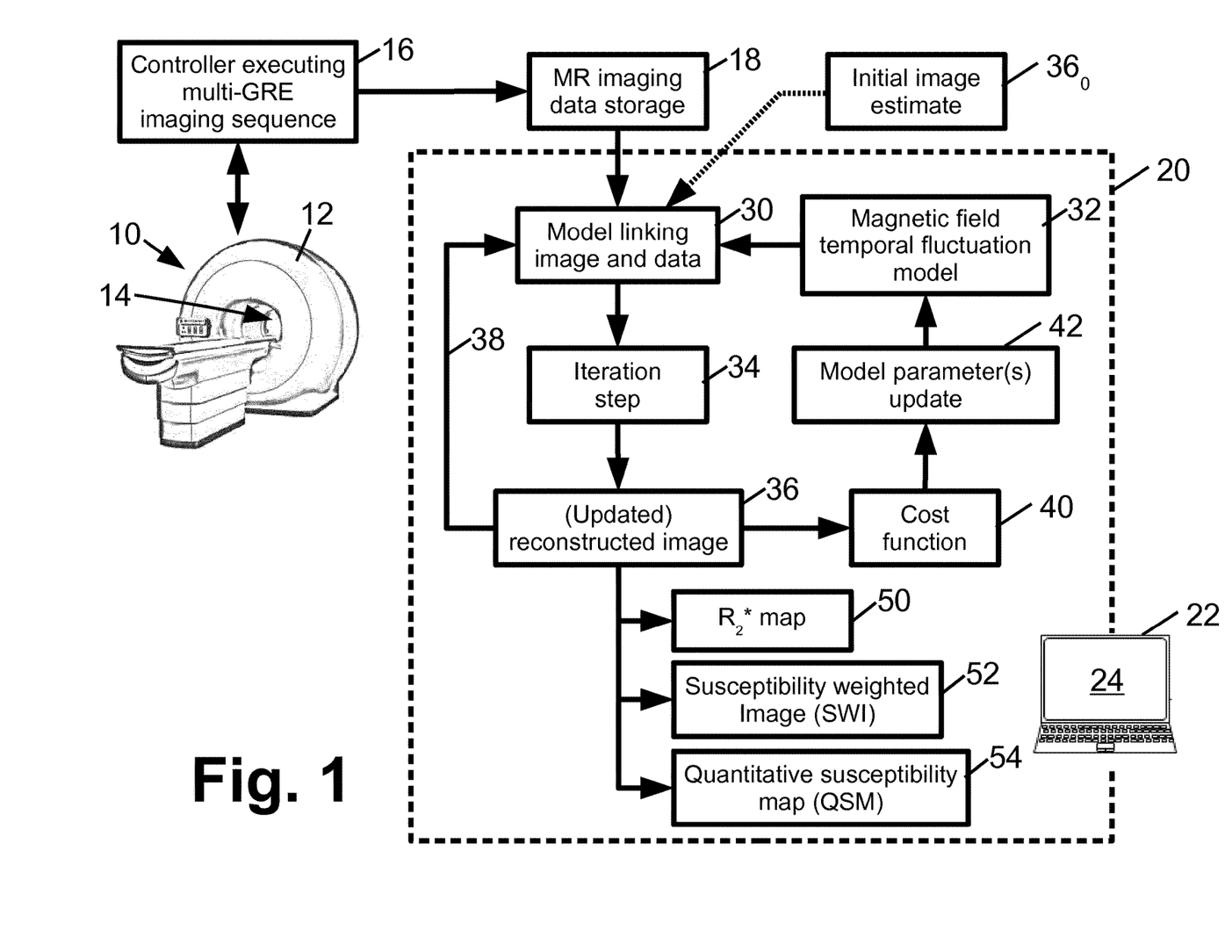
FIG. 1 diagrammatically shows a magnetic resonance (MR) imaging system including an MR scanner configured to perform multiple gradient echo (multi-GRE) imaging and a reconstruction device configured to reconstruct the multi-GRE imaging data to generate a reconstructed image with magnetic field fluctuation compensation.

With reference to FIG. 1, a magnetic resonance (MR) scanner 10 includes a housing 12 containing or having mounted thereon components (not shown) including a magnet (typically although not necessarily superconducting) arranged to generate a static ($B_0$) magnetic field in an examination region 14 (arranged as a horizontal bore 14 in the illustrative example) and a set of magnetic field gradient coils, e.g. for generating magnetic field gradients along orthogonal x, y, and z directions. To excite and read magnetic resonance, one or more radio frequency coils (RF coils, not shown) are employed, such as a head coil in the case of brain imaging. The MR scanner 10 further includes or is operatively connected with an MR controller 16 which is typically a computer or other electronic device including a microprocessor or other programmable electronic processor. In a typical operational paradigm, the superconducting magnet is ramped and stabilized to produce a (nominally) spatially and temporally constant $B_0$ magnetic field in the examination region 14, and the MR controller 16 controls the RF coil(s) to excite nuclear magnetic resonance at a magnetic resonance frequency in $^1H$ atoms or other target nuclei of an imaging subject (e.g. the brain of a medical patient in the case of magnetic resonance brain imaging), and controls the magnetic field gradient coils to spatially encode the excited magnetic resonance and/or generate gradient echoes and/or so forth, and controls the RF coil(s) to read the excited magnetic resonance. The resulting MR imaging data are stored in an MR imaging data storage 18, e.g. a hard disk drive, RAID disk array, a solid state drive (SSD), or the like.

In illustrative embodiments disclosed herein, the MR controller 16 is particularly programmed to operate the MR scanner 10 to execute a multiple gradient echo (multi-GRE) MR imaging acquisition sequence. In a GRE sequence, magnetic field gradients of opposite polarity are applied in sequence to generate a gradient echo; in multi-GRE this process is repeated two or more times to generate a corresponding two or more successive gradient echoes at respective echo times (TE) over the course of single repetition time (TR) of the multiple gradient echo MR imaging data acquisition. Multi-GRE sequences can be used, for example to perform rapid $R_2^*$-mapping, susceptibility weighted imaging (SWI), and/or quantitative susceptibility mapping (QSM) of the brain or another target organ or tissue. For example, in a typical SWI or QSM acquisition, each RF excitation pulse is manipulated to generate a plurality of gradient echoes at successive TE values with a given phase-encoding step over the TR for that RF excitation. This is repeated for successive phase encoding steps to acquire a 3D image $f(r, T_E)$ where r indexes spatial position and $T_E$ is the echo time (also sometimes denoted herein as TE). For a given spatial position, signal decay as a function of $T_E$ provides a measure of the $T_2^*$ decay (or, equivalently, $R_2^*$ relaxation), thus enabling $R_2^*$ mapping. SWI and QSM are related techniques that leverages the phase images, or the complex images including both magnitude and phase, at successive TE values together with image filtering and/or other image processing to produce susceptibility weighted images or quantitative susceptibility maps that (in brain imaging) provide clinically useful contrast for small hemorrhages, tumors exhibiting rapid angiogenesis, or certain other types of brain injuries or abnormalities. In these imaging techniques, long TE times (on the order of tens of milliseconds in some imaging sequences) are commonly used to enhance sensitivity to susceptibility effects. However, the combination of long TE times and the lack of spin refocusing in GRE imaging leads to $R_2^*$-mapping, SWI and QSM imaging being sensitive to image quality degradation due to temporal magnetic field fluctuations.

With continuing reference to FIG. 1, an MR image reconstruction device 20 is implemented via a suitably programmed computer 22 or other suitably programmed electronic data processing device. Moreover, an embodiment of the disclosed MR image reconstruction techniques may be embodied as non-transitory storage medium storing instructions readable and executable by the computer 22 to perform the disclosed reconstruction. The non-transitory storage medium may, by way of non-limiting illustrative example, be a hard disk drive or other magnetic storage medium, a solid state drive (SSD) or other electronic storage medium, an optical disk or other optical storage medium, various combinations thereof, or so forth. The MR image reconstruction device processes the multi-GRE imaging data stored in the storage 18 to generate a reconstructed MR image, which may in some embodiments comprise an $R_2^*$, SWI, and/or QSM image, that is displayed on a display 24. The MR image reconstruction device 20 performs iterative image reconstruction incorporating retrospective correction of the MR image for field-fluctuations induced by subject motion outside the FOV, e.g. caused by breathing. Parameters for the data correction are estimated for a given phase-encoding step (or, more generally, for a single TR) based on data for all acquired echoes simultaneously because physiological motion can be considered frozen during the short readout of the single TR.

As diagrammatically indicated in FIG. 1, the MR image reconstruction with field fluctuation correction employs a forward model 30 that connects the acquired multi-GRE imaging data (usually in the form of raw k-space data) to the reconstructed MR image. The forward model 30 includes a parameterized magnetic field fluctuation component 32 that compensates for temporal magnetic field fluctuation. Each iteration of the iterative reconstruction process entails an iteration step 34 that adjusts the reconstructed image to reduce the difference between the reconstructed image and the model data transformed to image space via an inverse Fourier transform to generate an updated reconstructed image 36. As an iterative process, the process flow 38 loops back to iteratively repeat the iteration step 34 to iteratively improve the reconstructed image 36 until a final image is reached (e.g. as defined by iteration-to-iteration improvement being below a threshold value, or per some other stopping criterion). Instead of operating in image space, the model 30 may instead operate in k-space, e.g. by applying a forward Fourier transform to the reconstructed image and comparing with the imaging data in k-space. To start the iterative process, an initial image estimate $36_0$ is employed, which may be a uniform image if no a priori information is available (and which advantageously avoids the possibility of introducing initial condition bias into the iterative reconstruction), or may be an a priori image estimate if such an image estimate is available.

The reconstruction process also iteratively adjusts parameters of the parameterized magnetic field fluctuation component 32 that compensates for temporal magnetic field fluctuation. To this end, a suitable cost function 40 is employed, which is dependent on partial derivatives of the reconstructed MR image 36 with respect to the parameters of the parameterized magnetic field fluctuation component 32 of the model 30. In a suitable embodiment, the cost function 40 measures the image quality of the reconstructed image 36 and its Jacobian with respect to the parameters of the parameterized magnetic field fluctuation component 32. In an update step 42, the parameters of the parameterized magnetic field fluctuation component 32 are changed (i.e. updated) to reduce the value of the cost function 40. Viewed another way, the forward model 30 is the image reconstruction pipeline, and may suitably include a coil-combination (for imaging employing a coil array) and a Fourier transformation and/or inverse Fourier transform. The cost function 40 may, for example, be implemented as a total variation cost function which is defined as the I-norm of the modulus of the image gradient (here, with respect to the parameters of the parameterized magnetic field fluctuation component 32). Other spatial gradient-based cost functions can be employed as the cost function 40. The parameters update step 42 may, for example, employ the Broyden-Fletcher-Goldfarb-Shanno (BFGS) algorithm, which is an iterative method for solving unconstrained nonlinear optimization problems.

With continuing reference to FIG. 1, the last update reconstructed image 36 is the final reconstructed image. This may be used directly, e.g. an image at a chosen TE value may be displayed. For clinical evaluation tasks, it may be more useful to process the final reconstructed image, e.g. to generate, and display on the display 24, an $R_2^*$ map 50, and/or a susceptibility weighted image 52 generated by susceptibility weighted imaging (SWI), and/or a quantitative susceptibility map 54 generated by quantitative susceptibility mapping (QSM).

In the following, an illustrative example is described. This example assumes the temporally varying magnetic field fluctuations to be compensated are spatially uniform. Under this assumption, the model 30 with the incorporated parameterized magnetic field fluctuation component 32 may be suitably implemented as:

$$f(r, T_E, \omega(k)) = \sum_c s_c^*(r) FT^{-1}\left(\exp(i\omega(k)T_E)\hat{f}_c(k)\right) \quad (1)$$

In the model of Equation (1), $FT^{-1}$ denotes the inverse Fourier-transform, $s_c^*(r)$ represents the coil sensitivities for the c-th channel (e.g. the c-th coil of a coil array used in the MR readout; the superscript "*" denotes complex conjugate), and $\hat{f}_c(k)$ is the k-space data measured for the c-th channel. The effect of a spatially uniform fluctuating field offset $\omega(t)$ on the k-space data acquired for a given echo-time TE is represented by the parameterized magnetic field fluctuation component 32 given by:

$$\tilde{f}_k = \exp(i\omega(k(t))T_E)\hat{f}_k \quad (2)$$

where $\tilde{f}_k$ is the ideal (i.e. field fluctuation-free) signal and $\hat{f}_k$ is the signal corrupted by temporally varying but (in this example) spatially uniform magnetic field fluctuation. The parameters are the terms $\omega(k(t))$. As it is assumed here that $\omega(k(t))$ is the same for all echoes, i.e. that the spatial fluctuation does not change appreciably over the repetition time TR, the parameters are written as $\omega(k)$ in Equation (1). The cost function 40 may, by way of non-limiting illustration, be the sum of the total variation (TV) for each echo, computed according to:

$$\sum_{echoes} TV(f(T_E)) = \sum_{echoes} \sum_r \sqrt{\left|\vec{G}f(T_E)\right|^2} \quad (3)$$

Here the operator $\vec{G}$ is the gradient operator respective to the parameters of the parameterized magnetic field fluctuation component 32, which is applied to the reconstructed image $f(T_E)$ for each echo TE (the reconstructed image with corruption given in Equation (1), but only for the echo $T_E$) and the results summed over all echoes by the outer summation. A suitable minimization algorithm, such as the limited memory BFGS algorithm, is employed to minimize the cost function of Equation (3) to find the optimal choice of the parameters $\omega(k)$.

Figure 2:
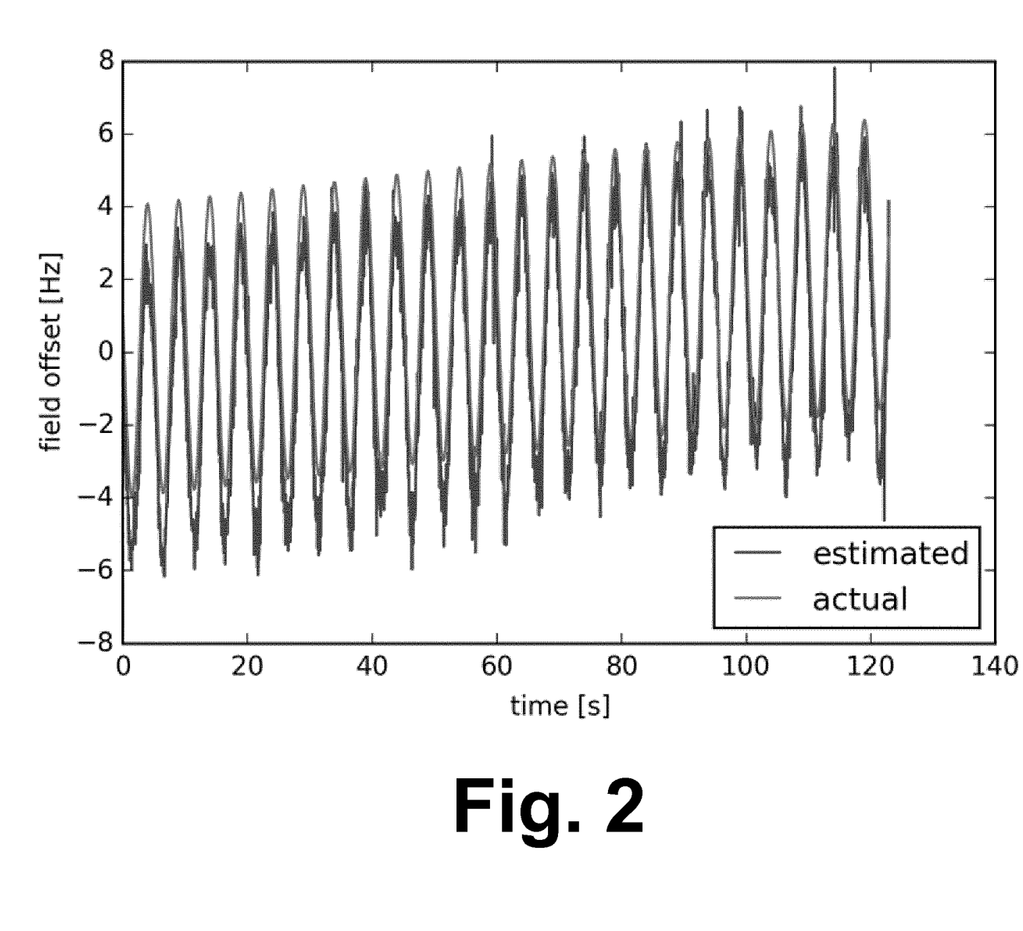
FIG. 2 plots k-space data modification corresponding to a sinusoidally varying field offset plus a linear drift for a numerical phantom experiment reported herein.
Figure 3:
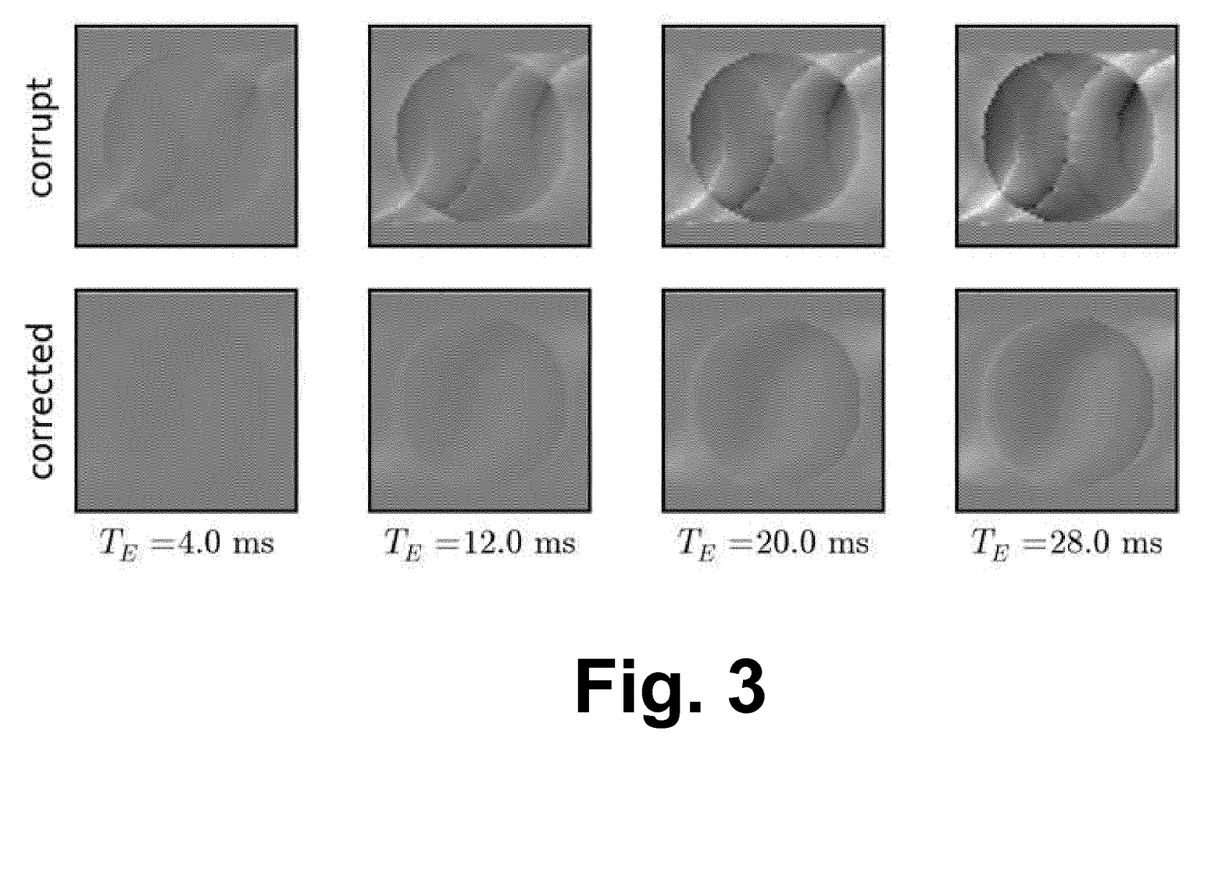
FIG. 3 presents numerical phantom reconstructed images generated by the numerical phantom experiment reported herein.

With reference to FIGS. 2 and 3, the example of Equations (1)-(3) was tested for a numerical phantom consisting of a sphere. Artificial coil sensitivities were used to generate k-space data at several echo times, with added noise corresponding to a signal to noise ratio (SNR) of 30. The k-space data was modified corresponding to a sinusoidally varying field offset plus a linear drift as shown in FIG. 2. The minimization algorithm was able to reduce artefacts arising from the field fluctuations, as illustrated in the numerical phantom results presented in FIG. 3, and approximately recover the field-fluctuations. FIG. 3 shows difference of magnitude images with respect to the ground-truth for data corrupted by field-fluctuations (upper row of FIG. 3) and for corrected data (lower row of FIG. 3) for a range of echo-times indicated in the lower column labels of FIG. 3.

The previous example assumes a temporally varying, but spatially uniform, magnetic field fluctuation. A more general illustrative example that relaxes the assumption of spatially uniformity of the temporal magnetic field fluctuation is next presented. Here, the (latest update) reconstructed image without corruption by field fluctuation is denoted as $f(r,T_E)$, which is a function of the spatial position r, and the echo-time $T_E$. The image corrupted by spatially and temporally varying field-fluctuations, $\omega(r,k(t))$, is then suitably represented by the model:

$$\tilde{f}(r, T_E, \omega(k(t))) = \sum_c s_c^*(r) FT^{-1}(FT(s_c(r) f(R, T_E) e^{i\omega(r,k(t))T_E})) \quad (4)$$

In Equation (4), FT is the Fourier-Transform, $FT^{-1}$ is the inverse Fourier-Transform, and $s_c(r)$ (and its complex conjugate $s_c^*(r)$) again models the coil sensitivities. In Equation (4), the exponential factor:

$$e^{i\omega(r,k(t))T_E} \quad (5)$$

is the parameterized magnetic field fluctuation component 32 which describes the effect on the measured magnetization caused by the additional off-resonance (that is, the temporally varying magnetic fluctuations $b_0$, which in this example are not assumed to be spatially uniform), so at any time t, $\omega=\gamma b_0$, where $\gamma$ is the gyromagnetic ratio, and $b_0$ is the field-fluctuation in Tesla. By definition, the average of $b_0$ over time is zero.

In the case of spatially homogenous field-fluctuations, the exponential term of Equation (5) can be taken outside the Fourier Transform, leading to the model of Equation (1) for spatially uniform temporally varying magnetic field fluctuations.

In the general case in which the magnetic field fluctuations are also assumed to vary spatially, a difficulty arises in that the magnetization distribution, which is imaged, must already be known. One approach for addressing this difficulty is to start with the images generated using the corrupted data and apply iterative reconstruction to determine the most suitable correction parameters. Another approach is to model the spatial component of the field-fluctuations. Typically, at most a linear spatial dependence of the magnetic field fluctuations along the three spatial axes (e.g. x, y, and z) is observed in multi-GRE brain imaging. A linear phase increase in image space translates into a shift proportional to the slope along the same axis in k-space. Accordingly, the effect of a linearly spatially varying field-fluctuation can be expressed by mathematically resampling the measured data in k-space. Using this model of the linear spatial component, Equation (4) can be rewritten as:

$$\tilde{f}(r, T_E, \omega(k(t))) = \sum_c s_c^*(r) FT^{-1}\left(R_{\omega(k(t)),T_E}\left(\hat{f}_c(k, T_E)\right)\right) \quad (6)$$

In Equation (6), the parameterized magnetic field fluctuation component 32 of Equation (5) has been written as the operator $R_{\omega(k(t)),T_E}$ which performs the multiplication with the exponential to model the homogenous field-fluctuations and k-space shifting for linearly varying phase contributions. By way of Equation (6), the computation of corrected images directly from the measured k-space data can be achieved, and therefore the efficient computation of the illustrative cost-function of Equation (3). Minimizing the cost-function yields an improved image and the estimated field-fluctuations as a function of time, as already described for the spatially uniform magnetic field fluctuations example.

It should be noted that when modeling the spatial variation as a linear variation along each of three orthogonal spatial axes, e.g. as per Equation (6), the linear variation along one or more of these axes could be modeled as having zero slope, i.e. could be modeled as spatially non-varying along that axis.

The foregoing worked-out examples are merely illustrative. Other models could be employed. For example, the illustrative model of Equation (1), (4), or (6) could be extended to include subsampling in k-space. As a specific example, SENSE reconstruction could be incorporated; more generally, other parallel imaging techniques.

While the total variation (TV) is used as the illustrative example of the cost function 40, other cost functions are contemplated as previously described. Further, while multi-GRE brain imaging, and more particularly $R_2^*$, SWI, and/or QSM brain imaging, are described herein as illustrative examples, it will be appreciated that the disclosed techniques for compensating temporally (and optionally also spatially) varying magnetic field fluctuations can be employed in any type of multi-GRE imaging of substantially any imaging subject, e.g. imaging of other anatomical regions of a human subject, or imaging of the brain or other anatomical region of a dog or cat or other veterinary subject, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions readable and executable by a computer to perform a magnetic resonance (MR) image reconstruction method comprising:
    performing an iterative reconstruction of multiple gradient echo MR imaging data to generate a reconstructed MR image, the iterative reconstruction using a model that links the MR imaging data and the reconstructed MR image wherein the model includes a parameterized magnetic field fluctuation component; and during the performing of the iterative reconstruction, updating parameters of the parameterized magnetic field fluctuation component of the model to optimize a cost function (40) dependent on partial derivatives of the reconstructed MR image with respect to the parameters of the parameterized magnetic field fluctuation component of the model.

2. The non-transitory storage medium of claim 1 wherein the parameterized magnetic field fluctuation component comprises $e^{i\omega(r,k(t))T_E}$ where $T_E$ is echo time of the MR imaging data at k-space location k(t) and ω(r,k(t)) comprises parameters of the parameterized magnetic field fluctuation component.

3. The non-transitory storage medium of claim 2 wherein the model that links the MR imaging data and a reconstructed MR image comprises:

$$\tilde{f}(r, T_E, \omega(k(t))) = \sum_c s_c^*(r) FT^{-1}(FT(s_c(r)f(r, T_E)e^{i\omega(r,k(t))T_E}))$$

where f(r,$T_E$) is the reconstructed MR image, $s_c$(r) and its complex conjugate $s_c^*$ (r) model MR receive coil sensitivities, FT denotes the Fourier transform, $FT^{-1}$ denotes the inverse Fourier transform, and $\tilde{f}$(r,$T_E$,ω(k(t))) is the reconstructed MR image corrupted by magnetic field fluctuation.

4. The non-transitory storage medium of claim 1 wherein the parameterized magnetic field fluctuation component models a spatial variation of magnetic field fluctuation as a linear variation along each of three orthogonal spatial axes.

5. The non-transitory storage medium of claim 1 wherein the parameterized magnetic field fluctuation component models the magnetic field fluctuation as a spatially uniform temporal magnetic field fluctuation and the parameterized magnetic field fluctuation component comprises $e^{i\omega(k)T_E}$ where $T_E$ is echo time of the MR imaging data at k-space location k and ω(k) comprises parameters of the parameterized magnetic field fluctuation component.

6. The non-transitory storage medium of claim 5 wherein the model that links the MR imaging data and a reconstructed MR image comprises:

$$f(r, T_E, \omega(k)) = \sum_c s_c^*(r) FT^{-1}\left(\exp(i\omega(k)T_E)\hat{f}_c(k)\right)$$

where $\hat{f}_c$(k) is the MR imaging data, $s_c^*$(r) models MR receive coil sensitivities, $FT^{-1}$ denotes the inverse Fourier transform, and f(r,$T_E$,ω(k)) is the reconstructed MR image corrupted by magnetic field fluctuation.

7. The non-transitory storage medium of claim 1 wherein the parameterized magnetic field fluctuation component models the magnetic field fluctuation as temporally constant over a single repetition time (TR) of an MR imaging data acquisition that generated the multiple gradient echo MR imaging data.

8. The non-transitory storage medium of claim 1 wherein the cost function comprises a total variation (TV) cost function.

9. The non-transitory storage medium of claim 1 wherein the updating comprises applying a Broyden-Fletcher-Goldfarb-Shanno (BFGS) algorithm to update the parameters of the parameterized magnetic field fluctuation component of the model to optimize the cost function.

10. The non-transitory storage medium of claim 1 wherein the stored instructions are further readable and executable by the computer to perform one or more of:
$R_2^*$ mapping using the reconstructed MR image to generate an $R_2^*$ map,
susceptibility weighted imaging (SWI) using the reconstructed MR image to generate an SWI image, and
quantitative susceptibility mapping (QSM) using the reconstructed MR image to generate a QSM map.

11. A magnetic resonance (MR) image reconstruction device comprising:
a computer; and
a non-transitory storage medium storing instructions readable and executable by the computer to perform an MR image reconstruction method comprising performing an iterative reconstruction of multiple gradient echo MR imaging data to generate a reconstructed MR image wherein the iterative reconstruction uses a model that links the MR imaging data and the reconstructed MR image and wherein the model includes a parameterized magnetic field fluctuation component having parameters that are updated during the iterative reconstruction:
wherein the iterative reconstruction includes updating the parameters of the parameterized magnetic field fluctuation component of the model during the iterative reconstruction to optimize a cost function dependent on partial derivatives of the reconstructed MR image with respect to the parameters of the parameterized magnetic field fluctuation component.

12. The MR image reconstruction device of claim 11 wherein the parameterized magnetic field fluctuation component comprises a function of ω(r,k(t))$T_E$ where $T_E$ is echo time of the MR imaging data at k-space location k(t) and ω(r,k(t)) comprise parameters of the parameterized magnetic field fluctuation component.

13. The MR image reconstruction device of claim 12 wherein the parameterized magnetic field fluctuation component comprises an exponential function of ω(r,k(t))$T_E$.

14. The MR image reconstruction device of claim 12 wherein the parameterized magnetic field fluctuation component models ω(r,k(t)) as having a linear variation along each of three orthogonal spatial axes.

15. The MR image reconstruction device of claim 11 wherein the parameterized magnetic field fluctuation component models the magnetic field fluctuation as a spatially uniform temporal magnetic field fluctuation.

16. The MR image reconstruction device of claim 15 wherein the parameterized magnetic field fluctuation component comprises a function of ω(k)$T_E$ where $T_E$ is echo time of the MR imaging data at k-space location k and ω(k) comprises parameters of the parameterized magnetic field fluctuation component.

17. The MR image reconstruction device of claim 11 wherein the parameterized magnetic field fluctuation component models the magnetic field fluctuation as temporally constant over each repetition time (TR) of the MR imaging data acquisition that generated the multiple gradient echo MR imaging data.

18. The MR image reconstruction device of claim 11 wherein the iterative reconstruction includes updating the parameters of the parameterized magnetic field fluctuation component of the model during the iterative reconstruction to optimize a cost function dependent on partial derivatives of the reconstructed MR image with respect to the parameters of the parameterized magnetic field fluctuation component.

19. The MR image reconstruction device of claim 11 further comprising:
a display operatively connected with the computer;
wherein the stored instructions are further readable and executable by the computer to perform quantitative susceptibility mapping (QSM) and to display a QSM map on the display.

20. The MR image reconstruction device of claim 11 further comprising:
a display operatively connected with the computer;
wherein the stored instructions are further readable and executable by the computer to display the reconstructed MR image on the display.

21. A magnetic resonance (MR) imaging device comprising:
an MR scanner configured to acquire multiple gradient echo MR imaging data; and
an MR image reconstruction device as set forth in claim 11 operatively connected to reconstruct the multiple gradient echo MR imaging data acquired by the MR scanner.

* * * * *